(12) United States Patent
Guo et al.

(10) Patent No.: US 11,334,995 B2
(45) Date of Patent: May 17, 2022

(54) HIERARCHICAL SYSTEMS AND METHODS FOR IMAGE SEGMENTATION

(71) Applicant: SHANGHAI UNITED IMAGING INTELLIGENCE CO., LTD., Shanghai (CN)

(72) Inventors: Yimo Guo, Lexington, MA (US); Shanhui Sun, Lexington, MA (US); Terrence Chen, Lexington, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 81 days.

(21) Appl. No.: 17/014,594

(22) Filed: Sep. 8, 2020

(65) Prior Publication Data

US 2021/0158511 A1    May 27, 2021

Related U.S. Application Data

(60) Provisional application No. 62/941,198, filed on Nov. 27, 2019.

(51) Int. Cl.
*G06T 7/00* (2017.01)
*G06T 7/11* (2017.01)
(Continued)

(52) U.S. Cl.
CPC .......... *G06T 7/0012* (2013.01); *A61B 5/0044* (2013.01); *A61B 5/1128* (2013.01); *A61B 5/7264* (2013.01); *G06F 3/0485* (2013.01); *G06K 9/6267* (2013.01); *G06N 3/0454* (2013.01); *G06N 3/08* (2013.01); *G06T 3/0093* (2013.01); *G06T 7/0014* (2013.01); *G06T 7/11* (2017.01); *G06T 7/248* (2017.01);
(Continued)

(58) Field of Classification Search
CPC .............. G06T 7/0012; G06T 7/11; G06T 2207/30048; G06K 9/6267; G06N 3/0454
See application file for complete search history.

(56) References Cited

U.S. PATENT DOCUMENTS 10,997,724 B2 *   5/2021   Ravishankar ........... G06F 17/15
2017/0109881 A1 *  4/2017   Avendi .................. G06T 7/0012
(Continued)

OTHER PUBLICATIONS

Zotti, Clement, et al. "Convolutional neural network with shape prior applied to cardiac MRI segmentation." IEEE journal of biomedical and health informatics 23.3 (2018): 1119-1128. (Year: 2018).*

(Continued)

*Primary Examiner* — Utpal D Shah
(74) *Attorney, Agent, or Firm* — Zhong Law, LLC

(57) ABSTRACT

Described herein are systems, methods and instrumentalities associated with image segmentation. The systems, methods and instrumentalities have a hierarchical structure for producing a coarse segmentation of an anatomical structure and then refining the coarse segmentation based on a shape prior of the anatomical structure. The coarse segmentation may be generated using a multi-task neural network and based on both a segmentation loss and a regression loss. The refined segmentation may be obtained by deforming the shape prior using one or more of a shape-based model or a learning-based model.

20 Claims, 6 Drawing Sheets

(51) Int. Cl.
  G06K 9/62    (2022.01)
  G06N 3/04    (2006.01)
  G16H 50/50   (2018.01)
  G16H 50/30   (2018.01)
  G16H 30/40   (2018.01)
  G06F 3/0485  (2022.01)
  G06T 11/20   (2006.01)
  G06T 13/80   (2011.01)
  G06T 19/00   (2011.01)
  G06T 7/55    (2017.01)
  G06T 7/73    (2017.01)
  G06T 7/246   (2017.01)
  A61B 5/00    (2006.01)
  A61B 5/11    (2006.01)
  G06T 3/00    (2006.01)
  G06N 3/08    (2006.01)

(52) U.S. Cl.
  CPC .............. *G06T 7/55* (2017.01); *G06T 7/73* (2017.01); *G06T 11/206* (2013.01); *G06T 13/80* (2013.01); *G06T 19/00* (2013.01); *G16H 30/40* (2018.01); *G16H 50/30* (2018.01); *G16H 50/50* (2018.01); *G06T 2200/24* (2013.01); *G06T 2207/10016* (2013.01); *G06T 2207/20081* (2013.01); *G06T 2207/20084* (2013.01); *G06T 2207/30048* (2013.01); *G06T 2210/41* (2013.01)

(56) References Cited

U.S. PATENT DOCUMENTS

| | | |
|---|---|---|
| 2019/0205606 A1* | 7/2019 | Zhou .................... G06N 3/0454 |
| 2019/0279361 A1* | 9/2019 | Meyer ..................... G06T 7/12 |
| 2021/0142539 A1* | 5/2021 | Ayush .................... G06T 11/00 |
| 2021/0299434 A1* | 9/2021 | Nsson ................. A61N 1/3603 |
| 2021/0401392 A1* | 12/2021 | Bengtsson ............ G16H 10/20 |

OTHER PUBLICATIONS

Ronneberger, Olaf et al.; "U-Net: Convolutional Networks for Biomedical Image Segmentation," Computer Science Department and BIOSS Centre for Biological Signalling Studies, University of Freiburg, Germany. <http://lmb.informatik.uni-freiburg.de/> (May 2015).

Cootes, T. F et al.; "Active Shape Models—Their Training and Application," Computer Vision and Image Understanding, vol. 61, No. 1, pp. 38-59, (Jan. 1995).

Cootes, Timothy F. et al.; "Active Appearance Models" IEEE Transactions on Pattern Analysis and Machine Intelligence, vol. 23, No. 6, (Jun. 2001).

* cited by examiner

HIERARCHICAL SYSTEMS AND METHODS FOR IMAGE SEGMENTATION

CROSS-REFERENCE TO RELATED APPLICATIONS

This application claims the benefit of Provisional U.S. Patent Application No. 62/941,198, filed Nov. 27, 2019, the disclosure of which is incorporated herein by reference in its entirety.

BACKGROUND

Medical imaging plays an important role in modern day healthcare services. With advanced imaging equipment such as medical resonance imaging (MRI) scanners, ultrasound scanners, X-ray machines, computed tomography (CT) scanners, or positron emission tomography (PET) scanners, an abundance of imagery data may be obtained and used to evaluate the conditions of human organs or tissues. For instance, automatic segmentation of the myocardium in a cine MRI image, may enable measurement of important cardiac diagnostic metrics such as radial and/or circumferential strains of the heart. As the volume of medical imagery data increases, the needs for automatic image processing tools also increase. One automatic image processing technique is image segmentation, which involves identifying an object of interest in a medical image and indicating the contours of the object the image to allow for a more focused analysis or study of the object. Aided by advanced computer vision and machine learning technologies, the accuracy and robustness of image segmentation has improved significantly in recent years. Many challenges remain in the field, however, due to present limitations of the technology (e.g., relating to image quality, computing power, etc.) and complexities of the human body.

SUMMARY

Described herein are systems, methods and instrumentalities associated with medical image segmentation. An image segmentation system as described herein may include one or more processors configured to implement a first neural network and a second neural network. The first neural network may be configured to receive an image that includes a visual representation of an anatomical structure such as a myocardium and generate a first segmentation of the anatomical structure based on the image. For example, the first neural network may be configured to generate the first segmentation by classifying a first plurality of pixels of the image as candidate pixels associated with the anatomical structure and estimating the respective distances of a second plurality of pixels from corresponding surface boundaries of the anatomical structure that are nearest to the pixels. The first neural network may determine a boundary of the anatomical structure based on the respective estimated distances of the second plurality of pixels from the corresponding surface boundaries and respective positions of the second plurality of pixels. Responsive to determining such a boundary, the first neural network may determine that one or more of the candidate pixels are located outside the boundary (e.g., the pixels may be part of the left ventricle rather than the myocardium) and exclude the one or more of the candidate pixels from the first segmentation. The first neural network may include a convolutional neural network (CNN) trained to perform the tasks described above, and the training may be conducted based on a segmentation loss (e.g., associated with classifying the first plurality of pixels as the candidate pixels of the anatomical structure) and a regression loss (e.g., associated with estimating the distances of the second plurality of pixels from corresponding surface boundaries of the anatomical structure).

The second neural network of the image segmentation system described herein may be configured to generate a second segmentation of the anatomical structure based on the first segmentation and a shape prior associated with the anatomical structure. The second neural network may initialize the shape prior based on the first segmentation a shape distribution of the anatomical structure and then deform the shape prior to derive the second segmentation. By initializing the shape prior based on the first segmentation, the image segmentation system may align the shape prior substantially with the first segmentation and prevent the segmentation task from being stuck in local minima. The deformation of the shape prior may be performed using a statistical model of shape or appearance that is associated with the anatomical structure, and the deformation may include the second neural network adjusting one or more parameters of the statistical model based on features (e.g., such as an intensity profile or a gradient) of the image. Alternatively or additionally, the deformation may be performed using a deep learning neural network, for example, by extracting features from the image near a vertex position of the shape prior via one or more convolutional layers, determining a direction and a step size for deforming the shape prior at the vertex position based on the extracted features (e.g., via regression layer), and moving the vertex position of the shape prior based on the determined direction and step size to fit the shape prior into the contour of the anatomical structure.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
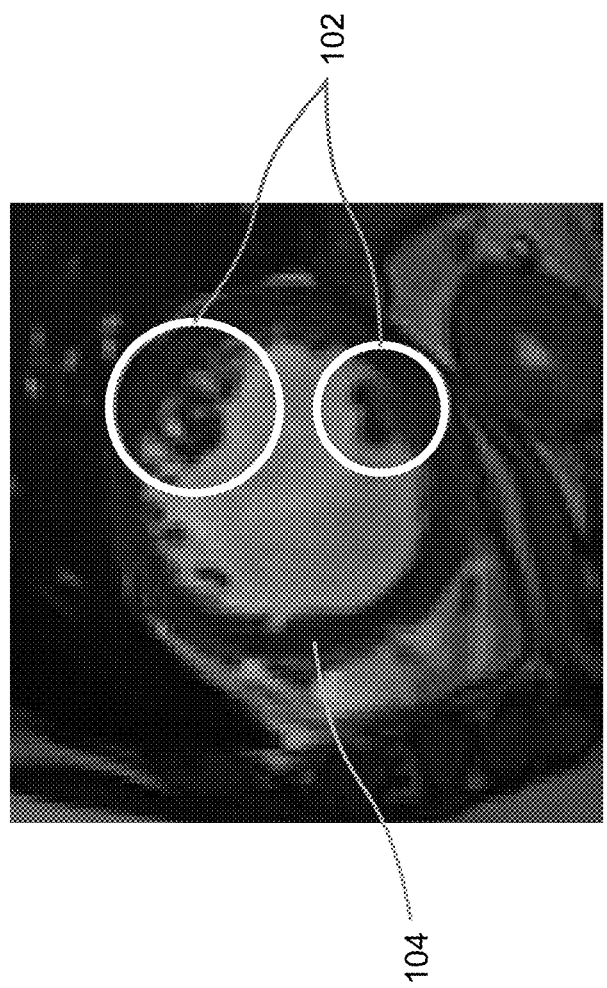
FIG. 1 is an example MRI image of the human heart illustrating visual similarities between parts of the left ventricle and the myocardium.

FIG. 1 is an example MRI image of the human heart illustrating visual similarities that may exist between parts of the left ventricle (LV) and the myocardium. The MRI image may be obtained via a cardiac MRI scan, for example, as part of a cine MRI. As shown in the example image, parts of the left ventricle such as the papillary muscle that are shown inside circles 102 of FIG. 1 may have similar appearances (e.g., in terms of image contrast, etc.) as the myocardium (e.g., indicated by the dark circular shape 104). The similarities may cause a conventional image segmentation system to misclassify parts of the left ventricle as belonging to the myocardium and produce unrealistic estimation results. The systems, methods and instrumentalities described herein may overcome the shortcomings of the conventional segmentation system and improve the accuracy and robustness of the segmentation results. Examples will be described herein with reference to the left ventricle or the myocardium of the human heart. It should be noted, however, that the techniques disclosed herein can be applied to the segmentation of any anatomical structure of the human body.

Figure 2:
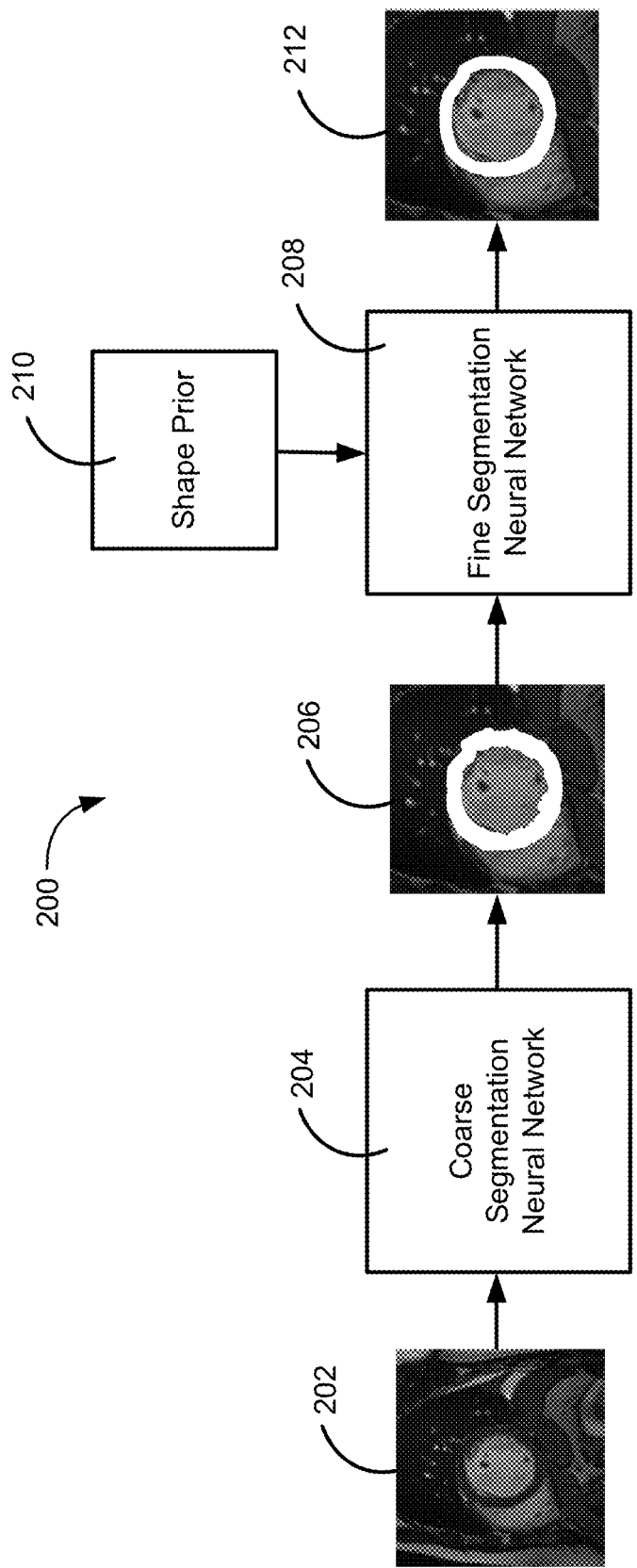
FIG. 2 is a block diagram illustrating an example image segmentation system as described herein.

FIG. 2 is a block diagram illustrating an example image segmentation system 200 as described herein. The image segmentation system 200 may be configured to receive an image 202 depicting an anatomical structure of the human body such as the human heart. The image 202 may be an MRI image obtained via a cardiac MRI, for example, as part of a cine MRI. The image 202 may be a colored image or a black-and-white image and may comprise a plurality of pixels with respective characteristics (e.g., in terms of brightness, contrast, intensity, gradient, etc.). The image segmentation system 200 may include a first neural network 204 (e.g., a coarse segmentation neural network) configured to receive the image 202 and generate a first segmentation 206 (e.g., a coarse segmentation) of the anatomical structure (e.g., the myocardium) based on the image 202. The first neural network 204 may include a deep convolutional neural network (DNN), a fully convolutional neural networks (FCNs), and/or another suitable type of neural networks that has learned, through a training process, how to identify one or more parts (e.g., one or more pixels) of the image 202 as belonging to the myocardium and segment (e.g., mark, separate, or otherwise distinguish) those parts from other parts of the image. The first segmentation 206 may correspond to a preliminary segmentation of the myocardium in the sense that the segmentation may still be rough and may be subject to further refinement by the image segmentation system 200. The first neural network 204 and the derivation of the first segmentation 206 will be described in greater detail below.

The image segmentation system 200 may include a second neural network 208 (e.g., a fine segmentation neural network) configured to receive the first segmentation 206 generated by the first neural network 204 and refine the first segmentation 206 based on a shape prior 210 of the anatomical structure and/or features of the image 202 to obtain a second segmentation 212 (e.g., a fine segmentation) of the anatomical structure. The refinement operation may include the second neural network 208 initializing the shape prior 210 based on a shape distribution of the anatomical structure (e.g., the probabilities of different shape variations of the anatomical structure in the general population) and the first segmentation 206 generated by the first neural network 204. The refinement operation may further include the second neural network 208 deforming the shape prior 210 based on one or more features of the image 202 to obtain the second segmentation 212. The second neural network 208 and the derivation of the second segmentation 212 will be described in greater detail below.

Figure 3:
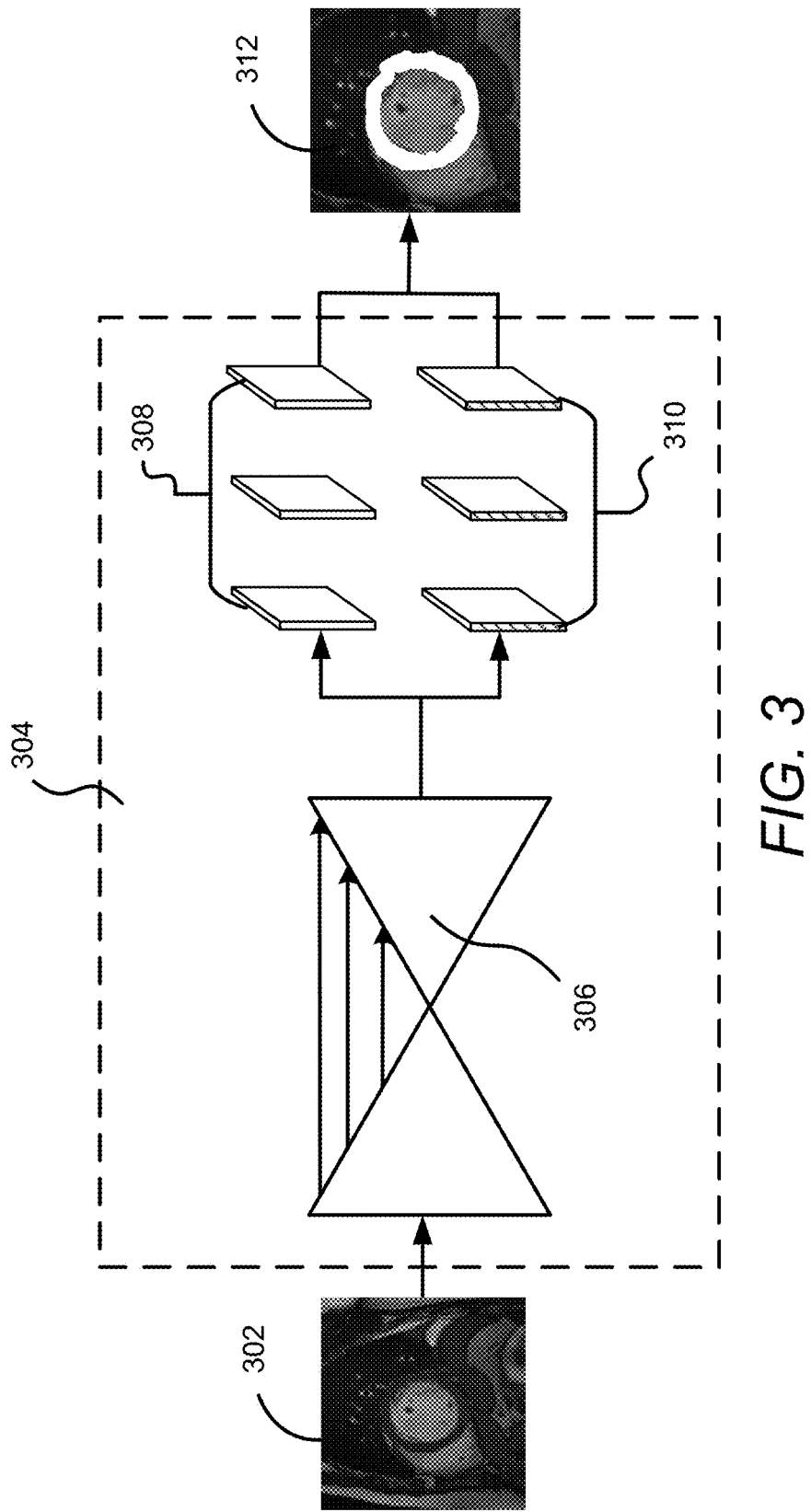
FIG. 3 is a block diagram illustrating the generation of a coarse segmentation of the myocardium using the example image segmentation system of FIG. 2.

By having a hierarchical structure as described above and utilizing both learning- and shape-based prediction techniques that complement each other, the image segmentation system 200 may produce robust segmentation results, for example, even in the presence of artifacts and noise in an MRI image such as those shown in FIG. 1 with the papillary muscle. FIG. 3 further illustrates the generation of a coarse segmentation of an anatomical structure (e.g., such as a myocardium) using the image segmentation system described herein, and FIG. 4 further illustrates the generation of a fine segmentation of the anatomical structure using the image segmentation system described herein.

Referring to FIG. 3, an image segmentation system as described herein (e.g., the image segmentation system 200 in FIG. 2) may receive an image 302 (e.g., the image 202 of FIG. 2) that includes a visual representation of an anatomical structure such as a myocardium. The image segmentation system may include a neural network 304 (e.g., the coarse segmentation neural network 204 shown in FIG. 2) configured to generate a segmentation of the myocardium based on visual features associated with the myocardium that the neural network 304 identifies in the image 302. The neural network 304 may include a convolutional neural network (CNN) such as a deep neural network or a fully convolutional neural network. The neural network 304 may include one or more convolutional layers, one or more pooling layers, and/or one or more fully connected layers that form various parts, branches, or sub-networks of the neural network 304. These parts, branches, or sub-networks may include, for example, a backbone network 306, a classification branch 308, and/or a regression branch 310. As will be described in greater detail below, the neural network 304 may perform multiple tasks (e.g., via the various parts, branches, or sub-networks) and therefore may operate as a multi-task neural network.

The backbone network 306 of the neural network 304 may be configured to identify, via convolution operation conducted through a plurality of convolutional kernels or filters, keypoints in the image 302 that collectively represent a feature or pattern in the image. The convolution operation may be followed by batch normalization and/or activation (e.g., using a rectified linear unit (ReLU) function), and the features extracted therefrom (e.g., in the form of one or more feature maps) may be down-sampled through one or more pooling layers and/or one or more fully connected layers of the neural network 304 (e.g., using a 2×2 window and a stride of 2) to reduce the redundancy and/or dimension of the features (e.g., by a factor of 2). The down-sampled features may subsequently go through an up-sampling process, e.g., via transpose convolution operation (e.g., using 3×3 transposed convolutional kernels with a stride of 2), to recover the spatial details associated with the extracted features.

One or more dense feature maps may be derived from the operation of the backbone network 306 and the feature maps may indicate the visual characteristics of various areas or pixels of the image 302. Based on these visual characteristics, a subset of the areas or pixels may be classified, e.g., by the classification branch 308 of the neural network 304, as belonging to the myocardium with respective probabilities, which may be indicated in a segmentation probability map produced by the classification branch 308.

The neural network 304 may be trained to optimize the parameters (e.g., weights associated with one or more layers of the neural network) that are associated with the segmentation task described above. The training may be conducted using a plurality of images of the myocardium and/or ground truth segmentation of the myocardium corresponding to each image. The parameters may be initially set to certain default values (e.g., which may be sampled from a probability distribution or based on parameter values of another neural network with a similar architecture). The training images may then be provided to the neural network 304 (e.g., via an input layer of the neural network). Responsive to receiving such a training image, the neural network 304 may process the image through the backbone network 306 and the classification branch 308 to extract features from the training image and classify one or more areas or pixels of the training image as being part of the myocardium. A segmentation loss may then be determined that indicates the difference between the classification results and a ground truth associated with the classification (e.g., an annotated segmentation of the myocardium). The segmentation loss may be determined, for example, using a segmentation loss function, which in turn may be based on one or more of a mean squared error (MSE), a L1 norm, a Dice ratio, cross entropy, etc., between the classification predicted by the neural network 304 and the ground truth. Responsive to determining the segmentation loss, the neural network 304 may adjust the parameters associated with the segmentation task based on the loss (e.g., based on a gradient descent of the segmentation loss function) with an objective of reducing the difference between the predicted classification and the ground truth.

The neural network 304 may also be configured to estimate, e.g., via the backbone network 306 and/or the regression branch 310, the respective distances of one or more voxels from corresponding surface boundaries of the myocardium. The one or more voxels may include those located inside the predicted myocardium and may correspond to respective pixels in the image 302. The surface boundary corresponding to each of the voxels may be the nearest surface boundary from that voxel, and the distance between the voxel and the surface boundary may be estimated as a 3D offset of the voxel from the surface boundary (e.g., based on differences between the x, y, z coordinates of the voxel and the x, y, z coordinates of a point on the surface boundary). The estimation may be performed, for example, using a regression layer (e.g., a fully-connected layer with a single node and/or a linear activation function) that may be part of regression branch 310 and based on features extracted from a training image (e.g., by the backbone network 306). As a result of the estimation, the neural network 304 may generate a 3D offset map (e.g., in addition to the segmentation probability map described above) that may indicate the estimated 3D offset of each of the one or more voxels from a corresponding nearest surface boundary. Since such a 3D offset map may indicate respective positions of the voxels and the distance of each voxel from its corresponding nearest myocardial surface, the 3D offset map may be used to determine a boundary of the myocardium and/or whether a voxel may be inside the myocardium or outside of the myocardium (e.g., be part of the left ventricle). Misclassification of an area or a pixel of the image (e.g., such as that shown in FIG. 1 with the papillary muscle) may then be corrected based on the estimated 3D offsets.

The neural network 304 may be trained to optimize the parameters (e.g., weights associated with one or more layers of the neural network) that are associated with the regression task described above. The training may be conducted using a plurality of images of the myocardium (e.g., the same set of images used for the segmentation training described above) and/or a ground truth that indicates the distances of one or more voxels from their nearest myocardial surface in each image. The parameters may be initially set to certain default values (e.g., which may be sampled from a probability distribution or based on parameter values of another neural network with a similar architecture). The training images may then be provided to the neural network 304 (e.g., via an input layer of the neural network). Responsive to receiving such a training image, the neural network 304 may process the image through the backbone network 306 and the regression branch 310 to extract features from the training image and estimate the distances of one or more voxels from respective myocardial surface boundaries that are nearest to the voxels. A regression loss may then be determined that indicates the difference between the regression results and the ground truth associated with the regression (e.g., annotated distances of the voxels to nearest myocardial surface boundaries). The regression loss may be determined, for example, using a regression loss function, which in turn may be based on one or more of a mean squared error (MSE), a L1 norm, etc., between the distances estimated by the neural network 304 and the ground truth. Responsive to determining the regression loss, the neural network 304 may adjust the parameters associated with the regression task based on the regression loss (e.g., based on a gradient descent of the regression loss function) with an objective of reducing the difference between the estimated distances and the ground truth.

By performing the segmentation task and the regression task described herein, the neural network 304 may produce a segmentation 312 of the myocardium that is less sensitive to artifacts, noise, and/or ambiguities in an input MRI image. For instance, although some tissues inside the left ventricle (LV) may have image contrast and/or intensity that are similar to the myocardium, the neural network 304 may be able to distinguish those tissues from the myocardium based on the 3D offsets estimated by the neural network (e.g., LV tissues may be located further away from a myocardium surface boundary than myocardial tissues). To further improve the accuracy and robustness of the segmentation, the image segmentation system described herein may include a second neural network (e.g., the neural network 208 of FIG. 2) that is trained to refine the segmentation results produced by the neural network 304.

Figure 4:
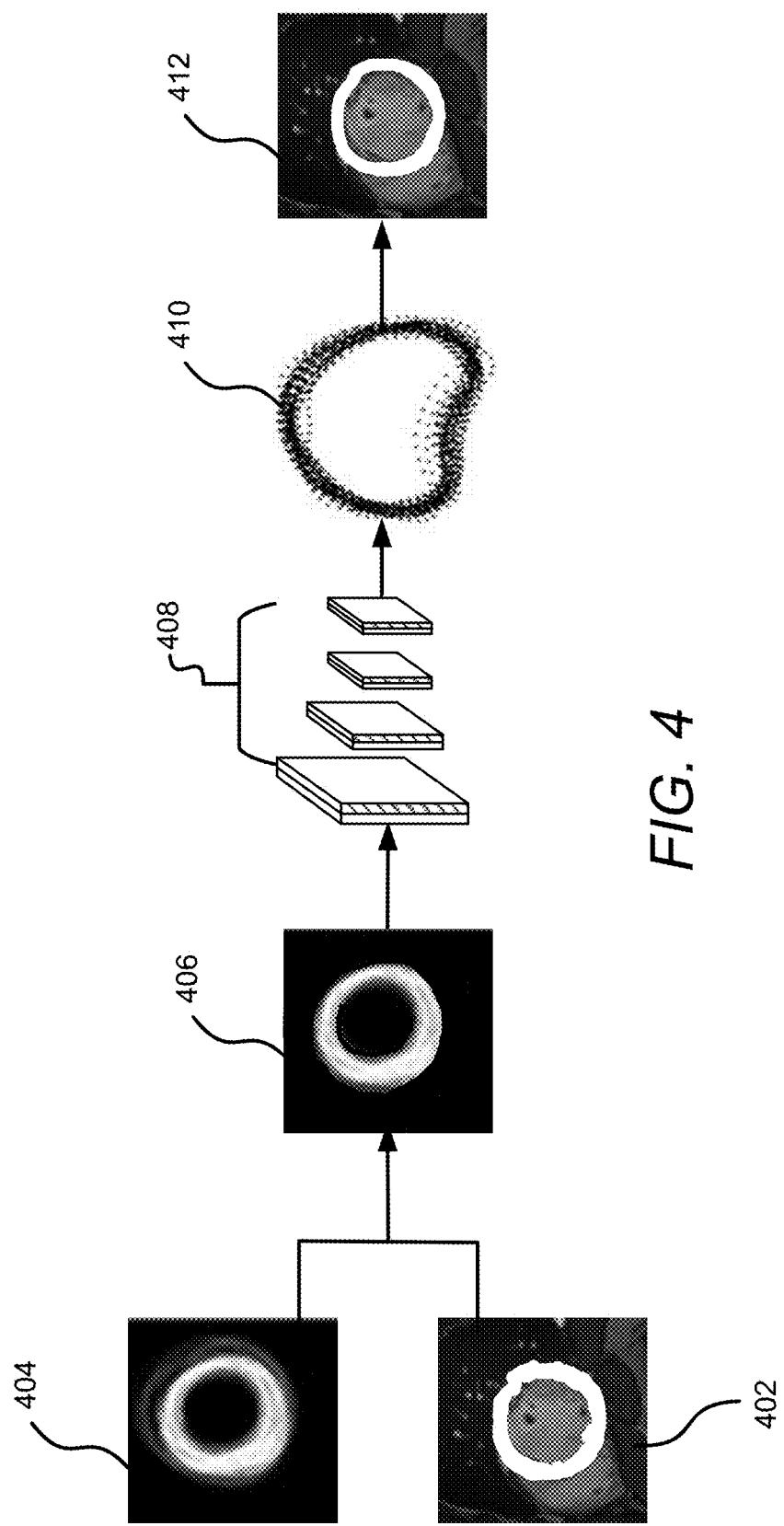
FIG. 4 is a block diagram illustrating the refinement of a coarse segmentation of the myocardium using the example image segmentation system of FIG. 2.

FIG. 4 illustrates a fine segmentation process that may be implemented by the image segmentation system described herein, for example, using a shape-based prediction model. Such a shape-based prediction model may utilize priori knowledge about the shape of the myocardium to regularize the segmentation predicted by the image segmentation system and consequently may overcome the artifacts, noise, and/or ambiguities included in an input MRI image. As shown in FIG. 4, the fine segmentation may be performed based on an input that includes a coarse segmentation 402 of the myocardium (e.g., such as the segmentation 312 generated by the neural network 304 in FIG. 3) and a shape distribution 404 of the myocardium. The shape distribution 404 may be predetermined, for example, based on known shape variations of the myocardium in the general population and as such may indicate the respective probabilities of the shape variations. In an initial stage of the fine segmentation, a shape prior 406 of the myocardium may be initialized based on the shape distribution 404 and the coarse segmentation 402. The initialization may be performed, for example, using rigid transformation techniques such as translation and rotation and/or using deformable transformation techniques such as B-spline deformation and/or diffeomorphic deformation. The initialization may be performed via a neural network (e.g., the neural network 408 described below) or another component of the image segmentation system (e.g., using image registration techniques). Since the coarse segmentation 402 already captures some characteristics of the myocardium, the initialization may bring the shape prior 406 to close approximation of the coarse segmentation 402 and ensure that the shape prior 406 resemble the contour of the myocardium, thus preventing the segmentation from getting stuck in local minima. Once the shape prior 406 has been initialized, it may be provided to a neural network 408 (e.g., the fine segmentation neural network 208 shown in FIG. 2), which may be configured to deform the shape prior 406 to fit the boundaries of the myocardium.

The deformation of the shape prior 406 may be performed using various prediction techniques and/or models. For instance, the neural network 408 may deform the shape prior 406 based on characteristics (e.g., features) of the input image that is associated with the deformation task. These characteristics may include, for example, an intensity profile of the input image, gradient information regarding the input image, geometric moments of the input image, specific characteristics of image patches surrounding one or more vertices of the shape prior, etc. From the characteristics, the neural network 408 may determine what parts of (e.g., one or more vertex positions) of the shape prior 406 may need to be expanded or contracted, and/or the directions and steps for performing the expansion or contraction.

In example implementations, the neural network 408 may be trained to learn a model (e.g., an active shape model or ASM) that represents the shape of the myocardium through a sequence of connected landmarks. Each of the landmarks may correspond to a distinguishable feature point in an image of the myocardium, and the neural network 408 may be trained to identify these feature points based on images of the myocardium that comprise annotated landmarks. For example, the neural network 408 may be configured to perform principal component analysis (PCA) on the training image set to determine an average shape of the myocardium and/or variations (e.g., deformations) to the average shape that may be acceptable (e.g., reasonably normal based on the shapes seen in the training data). Using such a shape model, the neural network 408 may begin with a starting hypothesis for the myocardium (e.g., the shape prior 406) and search around the current position of each modeled landmark in a new image to find a point nearby that best matches a texture expected at the landmark. Once such a point has been found, the neural network 408 may update the hypothesis for the myocardium by moving the landmark to the newly found point and repeat the process until the hypothesis and the image converge (e.g., as illustrated by 410 of FIG. 4) and a fine segmentation 412 is obtained. The neural network 408 may constrain (e.g., control) the movement of the landmark points during this search process based on what the neural network has learned from the training data as a normal myocardium contour, based on one or more geometric constraints (e.g., to prevent vertex crossing), etc.

In example implementations, the neural network 408 may be trained to learn a model (e.g., an active appearance model or AAM) that further considers the texture variations of the myocardium (e.g., in multiple regions rather than just near modeled landmarks) in addition to the shape of the myocardium in determining the myocardium's contour. The model may be learned using a training image set with annotated landmark points representing positions of key image features. The landmarks may be represented as one or more vectors and the neural network 408 may be configured to perform PCA on these landmark vectors to derive a statistical shape model. Additionally, the neural network 408 may also sample texture (e.g., intensity) information from the training images and apply PCA to the texture data to derive a statistical appearance model. The neural network may then concatenate the parameters of the shape and appearance models and apply a further PCA to the concatenated parameters to obtain a combined (e.g., shape and appearance) model that represents both shape and texture variability seen in the training image set. Using such a combined model, the neural network 408 may begin with a starting hypothesis for the myocardium (e.g., the shape prior 406, which may resemble the myocardium in terms of both shape and texture) and iteratively adjusting the model parameters to minimize the difference between a new image and one hypothesized by the model (e.g., as illustrated by 410 of FIG. 4) until the hypothesis and the image converge and a fine segmentation 412 is obtained.

In example implementations, the neural network 408 may be configured to determine the direction and/or step with which to deform the shape prior 406 based on image patches surrounding one or more vertex positions of the shape prior 406. In examples, the neural network 408 may regress the deformation direction and/or step using a regression model such as support vector regression or random forest. In examples, the neural network 408 may regress the deformation direction and/or step using a convolutional neural network (CNN) such as a deep neural network or a fully convolutional neural network that includes one or more convolutional layers, one or more pooling layers, and/or one or more fully connected layers. The convolutional layers may each include a plurality of convolution kernels or filters configured to extract visual features from an input image of the myocardium (e.g., image 302 in FIG. 3). The convolution operation may be followed by batch normalization and/or linear or non-linear activation to derive a plurality of feature maps that indicate the visual characteristics of the areas or pixels around one or more vertex positions of the shape prior 406. The neural network 408 may then determine the direction in which to expand or contract a vertex and/or the step size for the expansion or contraction based on the extracted characteristics (e.g., visual features), e.g., using a regression layer (e.g., a fully-connected layer with a single node and/or a linear activation function) of the neural network 408. Once the direction and/or step size are determined, the neural network may deform the shape prior 406 at a corresponding vertex position in accordance with the determined direction and/or step size, as illustrated by 410 of FIG. 4. The neural network may repeat this process for multiple vertex positions and/or through multiple iterations to obtain a fine segmentation 412 of the myocardium.

The neural network 408 may be trained to learn (e.g., optimize) the parameters (e.g., weights associated with one or more layers of the neural network) that are associated with determining the direction and/or step size of the deformation (e.g., the training may constitute a machine learning process). The training set may include a shape prior of the myocardium (e.g., which may be derived based on a shape distribution for the myocardium and/or a coarse segmentation of the myocardium). The training set may also include images of the myocardium and ground truth that indicates a fine segmentation of the myocardium. The parameters of the neural network 408 may be initially set to certain default values (e.g., which may be sampled from a probability distribution or based on parameter values of another neural network with a similar architecture). The shape prior and training images may then be provided to the neural network 408 (e.g., via an input layer of the neural network). Responsive to receiving the shape prior and a training image, the neural network 408 may process the image through the various convolutional, pooling and/or fully-connected layers of the neural network 408 to extract features from the training image and estimate respective directions and/or step sizes for deforming the shape prior at one or more vertex positions of the shape prior. The neural network 408 may then deform the shape prior 406 using the estimated directions and/or step sizes, determine a difference between the segmentation resulting from the deformation and the ground truth segmentation, and adjust the parameters of the neural network with an objective to minimize the difference. The difference may be determined based on a loss function such as a MSE or L1 normal based loss function, and the neural network may repeat the prediction, comparison and parameter adjustment process until one or more training termination criteria are satisfied (e.g., after completing a pre-determined number of training iterations, after the estimation loss falls below a predetermined threshold, etc.).

Figure 5:
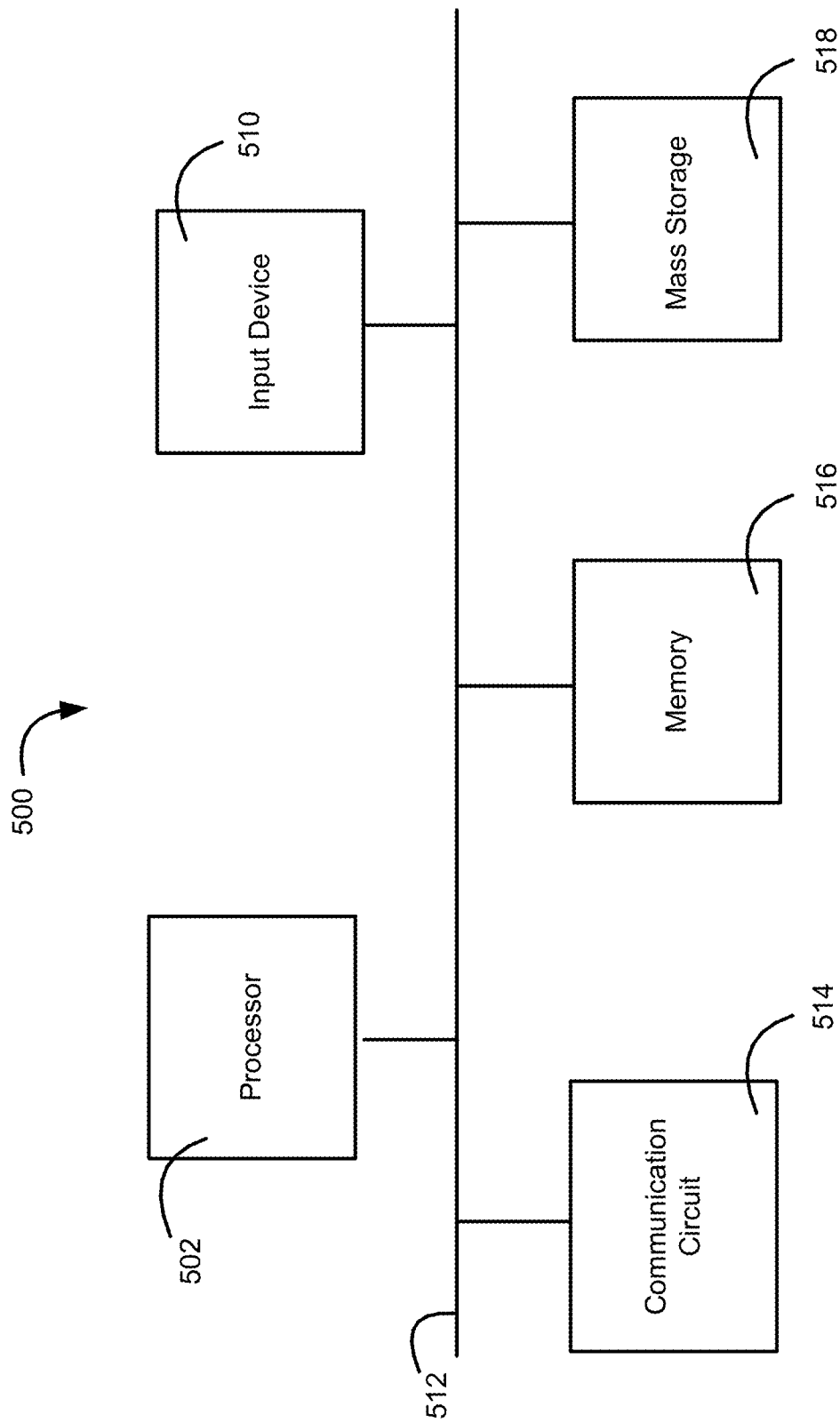
FIG. 5 is a block diagram illustrating example components of the image segmentation system of FIG. 2.

The image segmentation system (e.g., such as the system 200 in FIG. 2) described herein may be implemented using one or more processors, one or more storage devices, and/or other suitable accessory devices such as display devices, communication devices, input/output devices, etc. FIG. 5 is a block diagram illustrating an example image segmentation system 500 as described herein. As shown, the image segmentation system 500 may include a processor 502, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The image segmentation system 500 may further include a communication circuit 504, a memory 506, a mass storage device 508, an input device 510, and/or a communication link 512 (e.g., a communication bus) over which the one or more components shown in FIG. 5 may exchange information. The communication circuit 504 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 506 may include a storage medium configured to store machine-readable instructions that, when executed, cause the processor 502 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 508 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 502. The input device 510 may include a keyboard, a mouse, a voice-controlled input device, a touch sensitive input device (e.g., a touch screen), and/or the like for receiving user inputs to the image segmentation system 500.

It should be noted that the image segmentation system 500 may operate as a standalone device or may be connected (e.g., networked or clustered) with other computation devices to perform the functions described herein. And even though only one instance of each component is shown in FIG. 5, a skilled person in the art will understand that the image segmentation system 500 may include multiple instances of one or more of the components shown in the figure. Furthermore, although the examples are described herein with reference to various types of neural networks, various types of layers, and/or various tasks being performed by certain types of neural networks or layers, those references are made merely for illustration purposes and not meant to limit the scope of the disclosure. In addition, the operation of the example image segmentation system is depicted and described herein with a specific order. It should be appreciated, however, that these operations may occur in various orders, concurrently, and/or with other operations not presented or described herein. And not all operations that the image segmentation system is capable of performing are depicted and described herein, and not all illustrated operations are required to be performed by the system.

Figure 6:
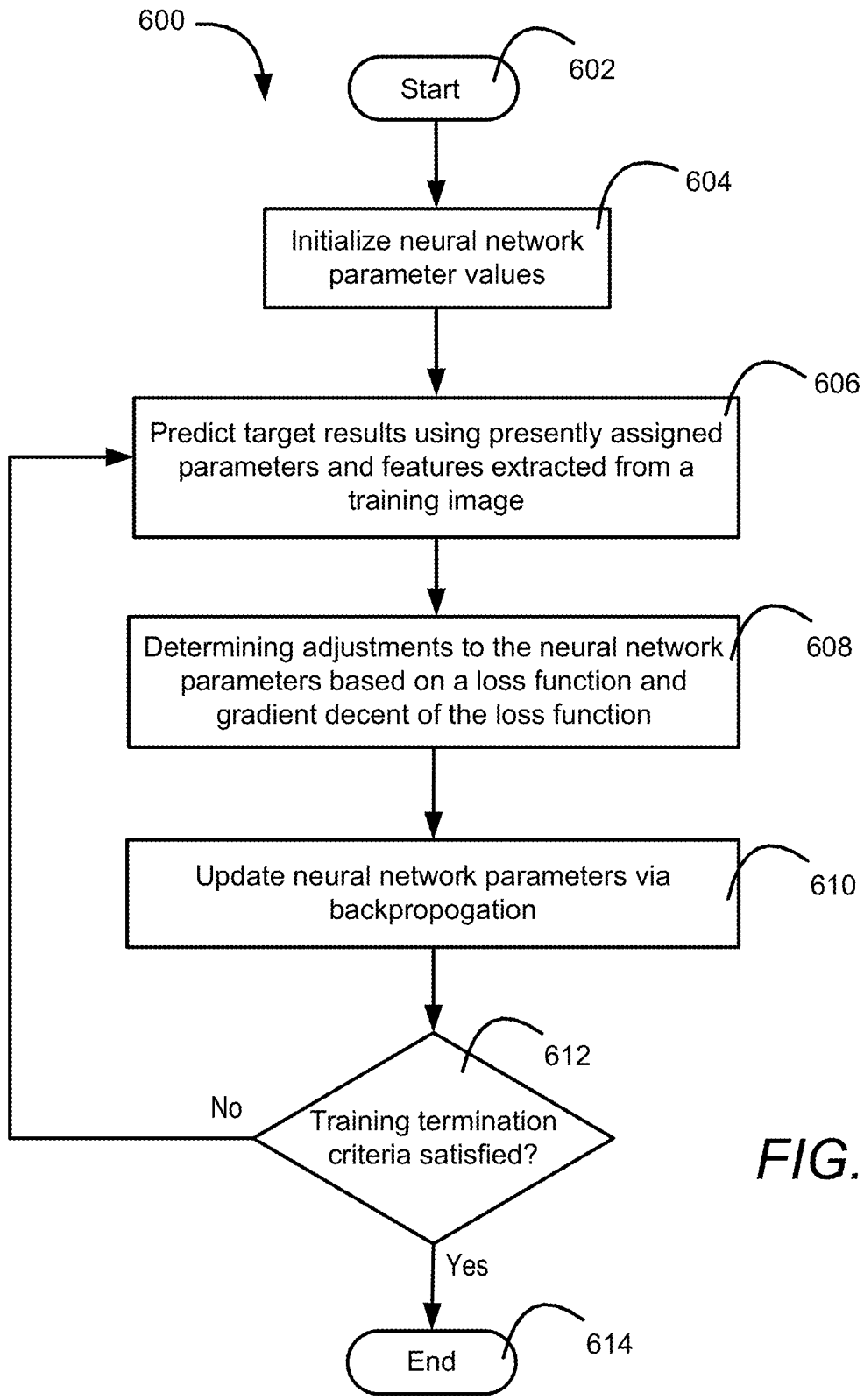
FIG. 6 is a flow diagram illustrating an example process for training the example image segmentation system of FIG. 2.

FIG. 6 is a flow diagram of an example process 600 for training a neural network as described herein (e.g., the neural network 304 of FIG. 3 or the neural network 408 of FIG. 4). The process 600 may start at 602 and, at 604, the neural network may initialize its operating parameters such as the weights associated with one or more filters or kernels of the neural network. The parameters may be initialized, for example, based on samples from one or more probability distributions or parameter values of another neural network with a similar architecture. At 606, the neural network may receive a training image, process the image through the various layers of the neural network, and make a prediction for a target result (e.g., a segmentation, a 3D offset, etc.) using presently assigned parameters. At 608, the neural network may determine adjustments to be made to the presently assigned parameters based on a loss function and a gradient descent (e.g., a stochastic gradient decent) associated with the loss function. For example, the loss function may be implemented based on a mean squared error (MSE) or an L1 norm distance between the prediction and a ground truth associated with the prediction. At 610, the neural network may carry out the adjustments to the presently assigned parameters, for example, via a backpropagation process. At 612, the neural network may determine whether one or more training termination criteria are satisfied. For example, the neural network may determine that the training termination criteria are satisfied if the neural network has completed a pre-determined number of training iterations, if the difference between the predicted values and the ground truth values is below a predetermined threshold, or if the change in the value of the loss function between two training iterations falls below a predetermined threshold. If the determination at 612 is that the training termination criteria are not satisfied, the neural network may return to 606. If the determination at 612 is that the training termination criteria are satisfied, the neural network may end the training process 600 at 614.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A system configured to segment medical images, comprising:
one or more processors configured to:
implement a first neural network, wherein the first neural network is configured to receive an image that includes a visual representation of an anatomical structure and generate a first segmentation of the anatomical structure based on the image;
implement a second neural network, wherein the second neural network is configured to generate a second segmentation of the anatomical structure based on the first segmentation and a shape prior associated with the anatomical structure, and wherein the second neural network is configured to initialize the shape prior based on the first segmentation and a shape distribution of the anatomical structure, the second neural network further configured to deform the shape prior to derive the second segmentation; and
indicate a contour of the anatomical structure based on the second segmentation.

2. The system of claim 1, wherein the initialization of the shape prior results in the shape prior being substantially aligned with the first segmentation.

3. The system of claim 1, wherein the second neural network is configured to deform the shape prior based on a statistical model of shape or appearance associated with the anatomical structure and the deformation comprises adjusting parameters of the statistical model in accordance with one or more features of the image.

4. The system of claim 3, wherein the one or more features are associated with an intensity profile of the image or a gradient of the image.

5. The system of claim 1, wherein the second neural network comprises one or more convolutional layers and the second neural network is configured to deform the shape prior by at least:
extracting features from the image near a vertex position of the shape prior via the one or more convolutional layers;
determining a direction and a step size for deforming the shape prior at the vertex position based on the extracted features; and
moving the vertex position of the shape prior based on the determined direction and step size.

6. The system of claim 5, wherein the second neural network further comprises a regression layer and the second neural network is configured to determine the direction and step size for deforming the shape prior via the regression layer and using a regression model derived through machine learning.

7. The system of claim 1, wherein the first neural network is configured to generate the first segmentation by at least:
classifying a first plurality of pixels of the image as candidate pixels associated with the anatomical structure;
for each of a second plurality of pixels, estimating a respective distance of the pixel from a surface boundary of the anatomical structure that is nearest to the pixel; and
excluding one or more of the candidate pixels from the first segmentation based on the estimated distances.

8. The system of claim 7, wherein the first neural network is configured to determine a boundary of the anatomical structure based on the respective estimated distances of the second plurality of pixels from the corresponding surface boundaries and respective positions of the second plurality of pixels, the first neural network further configured to exclude the one or more of the candidate pixels from the first segmentation based on a determination that the one or more of the candidate pixels are located outside the boundary of the anatomical structure.

9. The system of claim 7, wherein the first neural network comprises a convolutional neural network (CNN) trained to classify the first plurality of pixels as the candidate pixels of the anatomical structure based on a segmentation loss, the CNN further trained to estimate the distances of the second plurality of pixels from the corresponding surface boundaries based on a regression loss.

10. The system of claim 7, wherein the distances of the second plurality of pixels from the corresponding surface boundaries are determined as three-dimensional offsets of respective voxels that correspond to the second plurality of pixels from the corresponding surface boundaries.

11. The system of claim 1, wherein the anatomical structure is a myocardium.

12. A method for segmenting medical images, the method comprising:
receiving an image that includes a visual representation of an anatomical structure;
generating, via a first neural network, a first segmentation of the anatomical structure based on the image;
generating, via a second neural network, a second segmentation of the anatomical structure based on the first segmentation and a shape prior associated with the anatomical structure, wherein the generation of the second segmentation comprises initializing the shape prior based on the first segmentation and a shape distribution of the anatomical structure, and deforming the shape prior to derive the second segmentation; and
indicating a contour of the anatomical structure based on the second segmentation.

13. The method of claim 12, wherein the initialization of the shape prior results in the shape prior being substantially aligned with the first segmentation.

14. The method of claim 12, wherein the shape prior is deformed based on a statistical model of shape or appearance associated with the anatomical structure and the deformation comprises adjusting parameters of the statistical model in accordance with one or more features of the image.

15. The method of claim 14, wherein the one or more features are associated with an intensity profile of the image or a gradient of the image.

16. The method of claim 12, wherein the second neural network comprises one or more convolutional layers and the deformation of the shape prior comprises:
extracting features from the image near a vertex position of the shape prior via the one or more convolutional layers;
determining a direction and a step size for deforming the shape prior at the vertex position based on the extracted features; and moving the vertex position of the shape prior based on the determined direction and step size.

17. The method of claim 16, wherein the second neural network further comprises a regression layer and the second neural network is configured to determine the direction and step size for deforming the shape prior via the regression layer and using a regression model derived through machine learning.

18. The method of claim 12, wherein the first segmentation is generated by at least:
classifying a first plurality of pixels of the image as candidate pixels associated with the anatomical structure;
for each of a second plurality of pixels, estimating a respective distance of the pixel from a surface boundary of the anatomical structure that is nearest to the pixel; and
excluding one or more of the candidate pixels from the first segmentation based on the estimated distances.

19. The method of claim 18, wherein the first neural network is configured to determine a boundary of the anatomical structure based on the respective estimated distances of the second plurality of pixels from the corresponding surface boundaries and respective positions of the second plurality of pixels, the first neural network further configured to exclude the one or more of the candidate pixels from the first segmentation based on a determination that the one or more of the candidate pixels are located outside the boundary of the anatomical structure.

20. The method of claim 18, wherein the first neural network comprises a convolutional neural network (CNN) trained to classify the first plurality of pixels as the candidate pixels of the anatomical structure based on a segmentation loss, the CNN further trained to estimate the distances of the second plurality of pixels from the corresponding surface boundaries of the anatomical structure based on a regression loss.

* * * * *